United States Patent [19]

Jakubowicz et al.

[11] Patent Number: 5,271,896

[45] Date of Patent: Dec. 21, 1993

[54] PLUNGER AND DRIVER MECHANISM FOR AN ANALYZER

[75] Inventors: Raymond F. Jakubowicz, Rush; Russel H. Marvin; Johannes J. Porte, both of Webster, all of N.Y.

[73] Assignee: Eastman Kodak Company, Rochester, N.Y.

[21] Appl. No.: 49,020

[22] Filed: Apr. 16, 1993

[51] Int. Cl.$^5$ .................. G01N 21/00; G01N 35/00
[52] U.S. Cl. ................... 422/63; 221/226; 221/227; 422/50; 422/99; 422/104
[58] Field of Search ......... 221/226, 227, 258, 278; 422/63, 50, 99, 104

[56] References Cited

U.S. PATENT DOCUMENTS

| | | | |
|---|---|---|---|
| 4,260,581 | 4/1981 | Sakurada | 422/64 |
| 4,398,651 | 8/1983 | Kumpfer | 221/6 |
| 4,793,521 | 12/1988 | Steiner | 222/156 |
| 4,872,591 | 10/1989 | Konopka | 221/3 |
| 5,089,418 | 2/1992 | Shaw et al. | 422/63 |

FOREIGN PATENT DOCUMENTS 2176176 12/1986 United Kingdom ............ 221/258

Primary Examiner—James C. Housel
Assistant Examiner—Ramon Torres
Attorney, Agent, or Firm—Dana M. Schmidt

[57] ABSTRACT

A clinical analyzer moves a stack of slide or cup-like test elements into position for dispensing by a plunger and a driver featuring a housing around the plunger, a spring for biasing the plunger to project beyond the housing, a connection between the housing and the driver, and two sensors. The first sensor senses the initial movement of the housing and plunger toward the stack, and the second sensor senses movement of the plunger against the spring back into the housing upon contact with the stack.

10 Claims, 4 Drawing Sheets

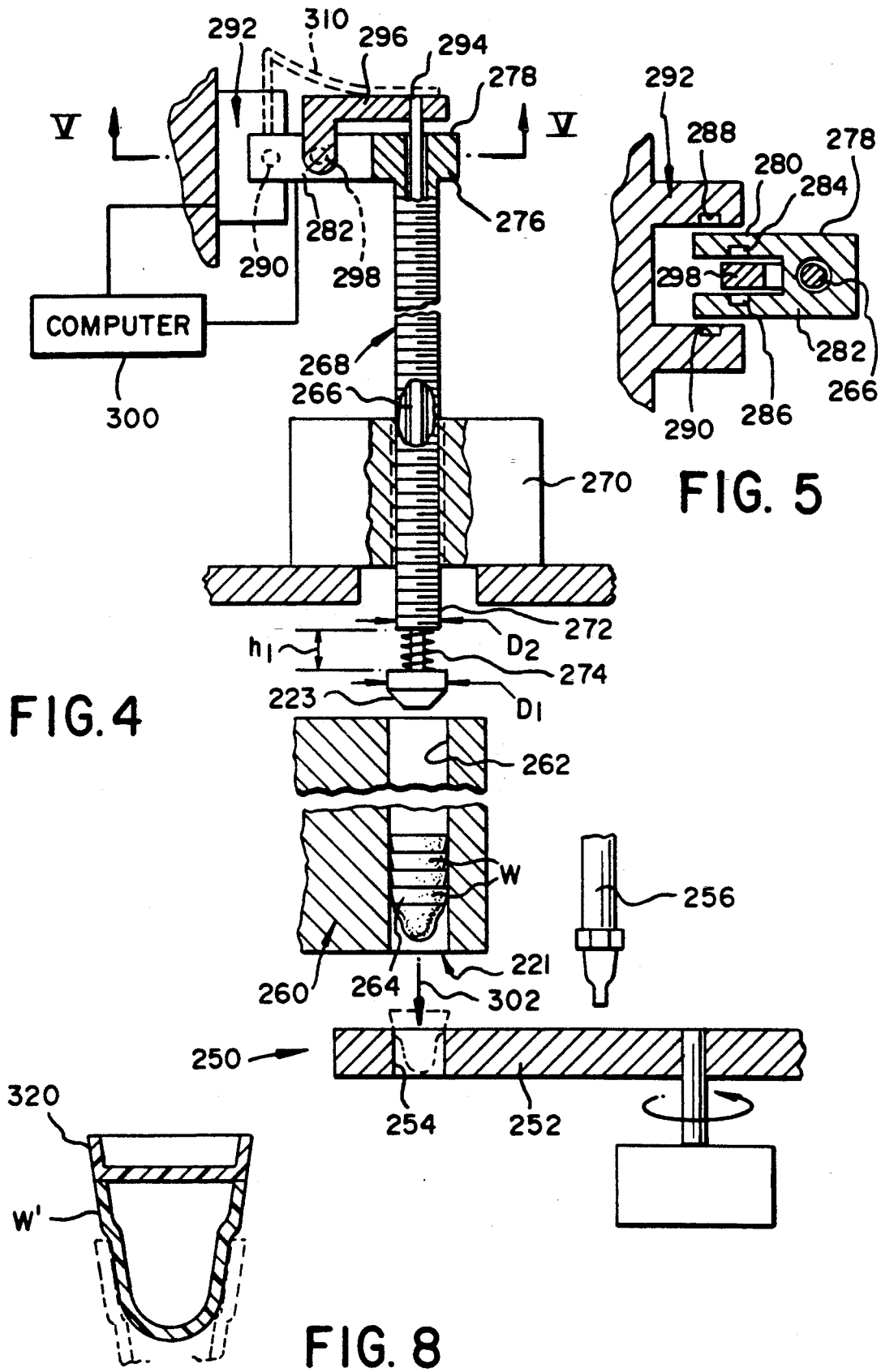

PLUNGER AND DRIVER MECHANISM FOR AN ANALYZER

FIELD OF THE INVENTION

This invention relates to a supply of test elements used in an analyzer, and particularly a plunger and its drive mechanism for advancing a stack of such elements to a dispensing location.

BACKGROUND OF THE INVENTION

In clinical analyzers for assaying patient sample liquids, it is conventional to provide a stack of test elements each of which is used to receive a portion of a patient sample liquid to do the assay, from a depositor. Such a stack features a plunger and a driver for the plunger, which press against one end of the stack to move its opposite end to a location for the dispensing of the test element into the analyzer. Means are also associated with the plunger, such as a bar code, for counting how far the plunger has moved, and hence how many test elements have been dispensed.

An example of this is taught by the slide cartridges and plungers therefor used in "Ektachem" analyzers, e.g., the "E250" analyzer. In such a case, a driver for the plunger comprises a complicated series of linking arms that pivot to convert rotary motion from a DC motor into what is almost linear motion of the plunger. A spring appropriately connected at one of the pivot points ensures an almost constant biasing force on the plunger.

Although such a mechanism has worked satisfactorily, it is less than ideal for several reasons. One is that its very complexity and large number of moving parts produces a low reliability. Another is all those parts lead to extra manufacturing costs. Still further, tolerance errors in all those parts can add up and thus lead to a departure from the desired "constant force" delivered by the plunger, or its desired linear movement. Finally, the linkage of the drive mechanism can produce vibrations which, because counting is via a bar code, produces a false count.

Thus, there has been a need prior to this invention to provide a simplified, truly linear drive to a plunger that contacts and pushes a stack of test elements, to more positively control the force exerted against the stack as well as the "count" that the mechanism measures of the remaining elements in the stack.

SUMMARY OF THE INVENTION

We have constructed a plunger and drive mechanism for an analyzer that overcomes the abovenoted problems.

More specifically, there is provided an analyzer for detecting analytes in a patient liquid deposited into a test element, the analyzer comprising a source of test elements including means for providing the test elements in a stack, a plunger for moving the stack linearly to a test element dispensing location, a driver operatively connected to the plunger to drive the plunger to and away from the stack, the driver including means for converting rotary motion into linear motion; and a patient liquid depositor for depositing liquid into a dispensed test element. The analyzer is improved in that the plunger further includes a housing within which the plunger is reciprocatingly mounted for linear movement, and biasing means for biasing the plunger normally outwardly of the housing but allowing the plunger to move into the housing against the action of the biasing means, a portion of the driver being mounted on the housing; and sensing means for sensing when the plunger has moved into the housing against the action of the biasing means, so that a signal can be generated that the plunger has encountered the stack.

Accordingly, it is an advantageous feature of the invention that a plunger and drive mechanism are provided in an analyzer, which ensure the plunger moves in a linear fashion, with constant force on the stack, while providing an accurate count of the test elements remaining in the stack.

It is a related advantageous feature that such a plunger and drive mechanism are provided using a minimum of parts and expense.

Other advantageous features will become apparent upon reference to the following Detailed Description, when read in light of the attached drawings.

BRIEF DESCRIPTION OF THE DRAWINGS

FIG. 4 is a fragmentary elevational view, partly in section, showing the plunger and drive mechanism as it is used with another embodiment of the invention (for wet assays);

FIG. 5 is a fragmentary section view taken generally along the line V—V of FIG. 4;

FIG. 8 is an elevational view in section of one embodiment of the top portion of a stack of test elements used in the embodiment of FIGS. 4-7.

DESCRIPTION OF THE PREFERRED EMBODIMENTS

The description which follows features the preferred embodiments, in which the plunger is demonstrated in its use for both so-called "dried" slide test elements of the type available from Eastman Kodak Company under the trademark "Ektachem" slides, and reagent cups used in wet assays with liquid reagents. In either case, patient sample liquid is deposited into them since, in the case of the slide elements, it is absorbed into or received by them in one form or another. In those contexts, preferred additional analyzer features are also described. In addition, the invention is useful regardless of the form of the test elements involved or the related analyzer apparatus, so long as the test elements are stored as, and the plunger operates on, a stack of them.

Orientations such as "up", "above", "underneath" and the like refer to orientations of parts in their intended use.

Figure 1:
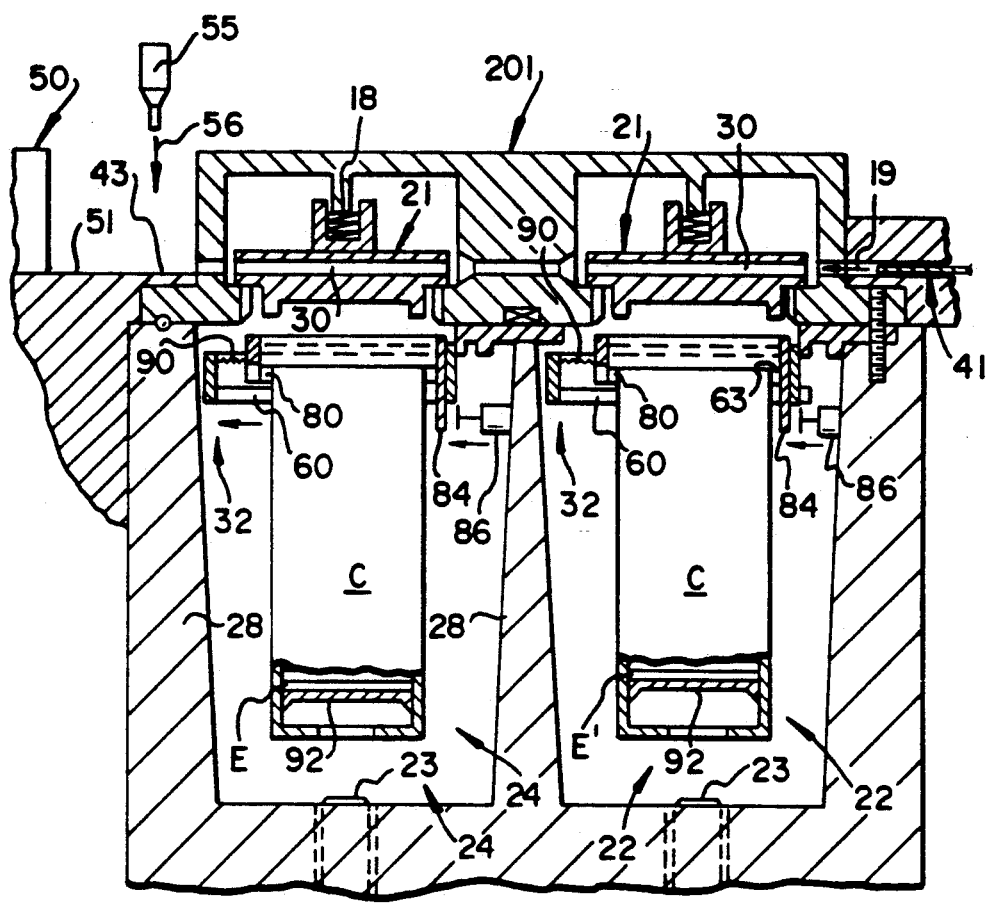
FIG. 1 is a fragmentary elevational view in section of an analyzer illustrating one embodiment of the use of the invention.

In one embodiment of the invention, an analyzer 10, FIG. 1, utilizes dried slide test elements E and E' (of two different types), preferably held in place as a stack by means of a cartridge C which surrounds them. Although other mounting arrangements are possible for the cartridges, the cartridges can be provided, for example, in concentric tracks 22 and 24, separated by a wall 28. In this arrangement, they are removably supported on the top of movable rings 32, each for upward movement by plungers 23 into a slide dispensing position against a respective platen 21 that is biased by a spring 18 downwardly in a housing 201. Each platen is slotted at 30 to allow a slide element to be pushed through from a cartridge in the other track by a pusher blade 41, arrow 19. The movement of the slide element proceeds, via the pusher blade, to a station 43 on support 51 where a depositor 55 deposits some patient sample liquid, arrow 56, prior to the slide element being inserted into an incubator 50. When a cartridge C is depleted, it is dumped from its ring 32 by a mechanism 84, 86 and 90. The details of the dumping mechanism, and indeed of all the features shown in FIG. 1, are conventional and are described in greater detail in commonly-owned U.S. Pat. No. 5,089,418.

An anti-backup plate 92 is conventional with such cartridges at the bottom of each stack. This platen moves up with the bottom-most slide element E or E', and stays at its last position until plunger 23 pushes it up further. This ensures that the remaining slides do not fall to the bottom when the plunger for that cartridge is temporarily pulled downward to allow another cartridge from either that same track (not shown), or the adjacent track, to be used to supply a slide element.

The retention of the slides at the top of the cartridge means that the distance the plunger 23 has to move upward from a home position (the down-most position) until it contacts the anti-backup plate 92 and hence the stack, is a measure of the number of test elements used, and hence the number remaining, as will become apparent.

Figure 2:
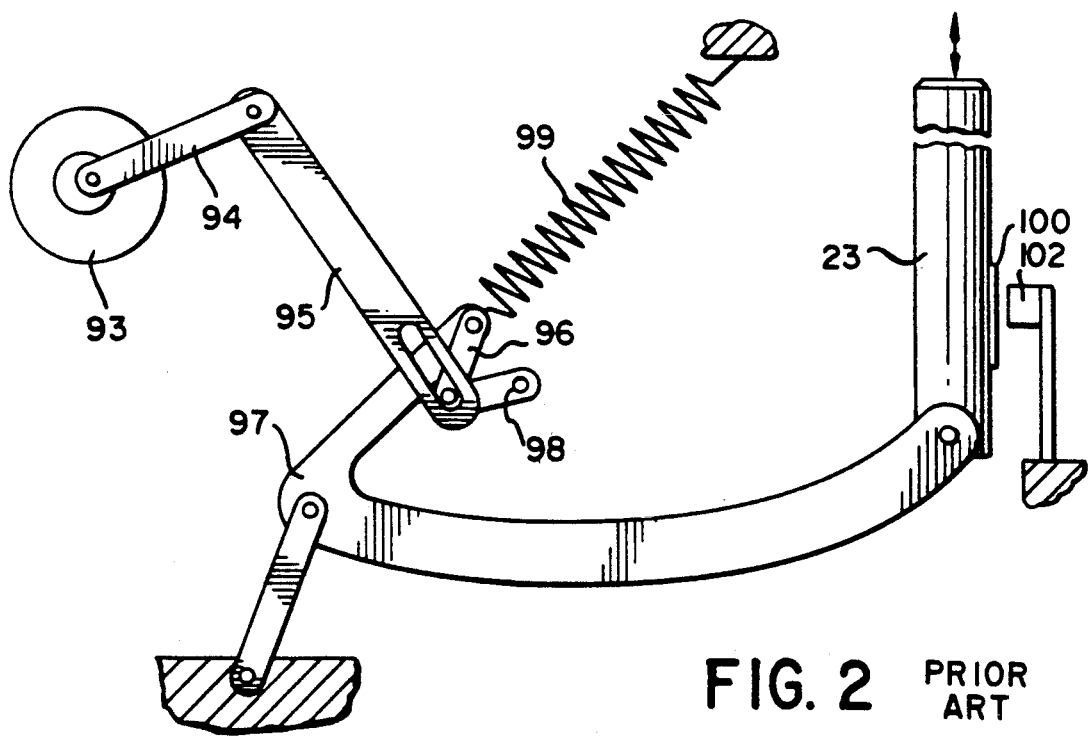
FIG. 2 is a partially schematic, elevational view showing the prior art operation of the plungers of FIG. 1.

FIG. 2 illustrates the prior art method described in the "Background" for driving plungers 23 linearly. A motor 93 turns a shaft on which is mounted a series of levers 94-97 that convert the rotary motion of motor 93 into approximate linear motion. Lever 97 is pivotally fixed at 98 and attached to the plunger, and a spring 99 is judiciously connected to lever 97 to exert a more or less constant upward force on plunger 23. To sense the distance traveled by the plunger and hence the number of slide elements already used (and the number remaining), a bar code 100 is formed on the side of the plunger for scanning by reader 102.

This construction has the drawbacks mentioned above in the "Background", not the least of which is at least six moving parts connecting the plunger to motor 93.

Figure 3A:
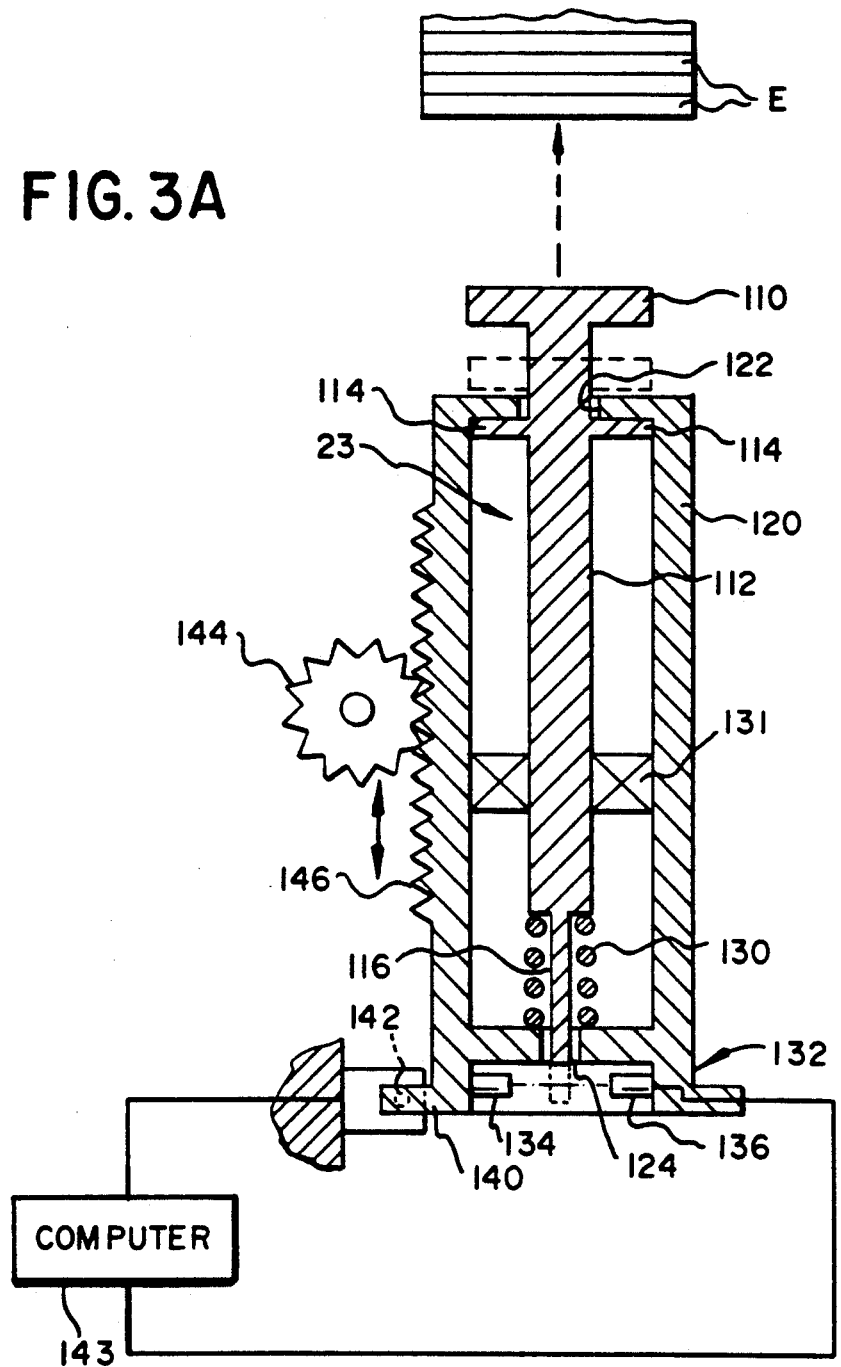
FIG. 3A is a fragmentary elevational view, in section, of the improved plunger and drive mechanism of this invention as it is used with the embodiment of FIG. 1 (dried assays).

In accordance with the invention, a greatly simplified driver is provided in FIG. 3A. Plunger 23 comprises a projecting head 110, a shank portion 112, stop shoulders 114, and a flag portion 116. Shank portion 112 and stop shoulders 114 are confined within a housing 120 that is apertured at 122, 124 at its two opposite ends. Head 110 of plunger 23 projects through aperture 122, and flag portion 116 projects into, and out of when depressed, aperture 124. To bias plunger 23 upward so that flag portion 116 normally does not project out aperture 124, a compression spring 130 is mounted between plunger 23 and the housing. Annular bearing 131 is used to keep plunger 23 centered.

Outside of aperture 124 is a sensing portion 132 of housing 120 on which is mounted a suitable sensor, such as an infrared diode and detector 134, 136 that emits and detects a beam of light traversing aperture 124. A shoulder 140 on portion 132 acts as a flag to trigger a similar second sensor 142 fixed to the analyzer. Both sensors 136 and 142 are connected to a computer 143 to calculate the number of slide elements remaining in a stack.

To drive housing 120, a pinion gear 144 is driven by a suitable stepper motor (not shown). A rack gear 146 is mounted on the side of housing 120 to engage gear 144. Alternatively, a worm gear arrangement is also useful.

In operation, head portion 110 of plunger 23 is biased upwardly, as shown by the solid line position, until plunger 23 contacts the bottom of the stack of elements E (actually, the anti-backup platen, not shown) remaining at the top of a cartridge (not shown). This occurs because gears 144 and 146 act to drive housing 120 and biased plunger 23 into contact. As soon as housing 120 starts upward shoulder portion 140 uncovers sensor 142 and computer 143 registers a "zero" or home position, so that all half-steps, or whole steps if desired, advanced by the stepper motor for gear 144 can be counted. At the moment of contact between head portion 110 and the stack of elements, gear 144 continues to drive to force the cartridge and its stack into contact with platen 21, FIG. 1, with spring 18 fully compressed. At this point, plunger 23 becomes stationary, so that flag portion 116, FIG. 3A, breaks the beam between diode 134 and detector 136. A signal is sent to computer 143, which stops driving gear 144 and registers that the stack of slide elements E has been contacted. The number of half- or whole steps the stepper motor has advanced is then calculated by the computer as the number of slide elements used up, and by subtraction, the amount remaining. Thus, it is no longer necessary to use a bar code label on the plunger.

As long as head portion 110 is prevented from advancing upwardly by a cartridge, spring 130 in its compressed state delivers a constant expansion force against plunger 23 and the stack of slide elements, regardless of the number of slide elements present.

ALTERNATE EMBODIMENTS

Figure 3B:
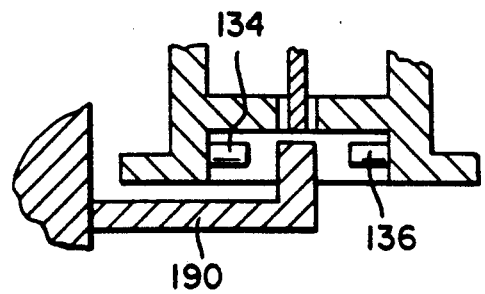
FIG. 3B is a fragmentary view in section similar to that of FIG. 3A, but of an alternate embodiment.

An alternative to the use of second sensor 142 and shoulder 140 is to convert sensor 142 into a fixed flag 190, FIG. 3B, which projects into the path of the beam between 134 and 136 when the plunger and housing are in the home position, shown in FIG. 3B.

Still further, it is not necessary that the plunger be restricted for use with a stack of dried slide elements. Nor, for that matter, need it be used only to push the stack upwardly. FIGS. 4-8 illustrate its use in a wet assay analyzer, so-called because the reagents are used in liquid, rather than dried, form. Furthermore, the stack of test elements is pushed downwardly, rather than upwardly, for ejection of a test element at the bottom, rather than the top, of a stack. Because the assay is a wet assay, the test elements now comprise a reagent cup "W", FIG. 4.

Any wet assay analyzer can be used with this invention, and there are many such available in the prior art. Conventionally, such an analyzer dispenses a reagent cup W from a dispensing location 221, into an incubator 250 comprising, for example, a rotor 252 with holding apertures 254, that rotates the cup W into position under a patient liquid depositor 256, to at least one reagent liquid depositor (not shown), and then to a read station (also not shown). (Stations downstream of the dispensing location 221 are not part of the invention and are not described further.)

It is conventional when supplying such cups W to stack them, one inside the other, as shown, in a holder 260 apertured at 262. Inside aperture 262 at location 221 a lip 264 is provided to act as a retainer to retain the stack against falling out. Lip 264 can be either a complete annular ring in aperture 262, or only fragments thereof. A plunger 223 is also conventionally employed at the opposite end of the stack to apply driving pressure downward on the stack.

In accordance with the invention, the driving of plunger 223 is achieved in the following fashion:

Plunger 223 is mounted at one end of a rod 266 that loosely fits within a housing 268, which is preferably a lead screw. Housing 268 in turn is driven by a stepper motor in a linear actuator 270 fixed to the analyzer. Bottom end 272 of housing 268 is spaced away from plunger 223, preferably by a compression spring 274. Opposite end 276 of housing 268 terminates in a collar 278 having a split yoke 280, 282, FIG. 5, between which is mounted a first sensor comprising, e.g., an infrared diode 284 and detector 286. Additionally, yoke 280, 282 acts as a flag for a second sensor comprising a similar diode 288 and detector 290 fixed to the analyzer on portion 292.

The end 294 of rod 266, FIG. 4, that is opposite to plunger 223, extends out beyond and above collar 278 on housing 268. An L-shaped flag finger 296 is affixed to end 294, portion 298 thereof normally projecting into the beam of light emitted between diode 284 and detector 286, FIG. 5.

Because housing 268 also advances into aperture 262, its outside diameter $D_2$, FIG. 4, is preferably less than outside diameter $D_1$ of plunger 223.

A computer 300 keeps track of and controls the operation of the plunger and its drive mechanism.

In operation, the home position of collar 278 is that shown in FIG. 4, that is, in its fully "up" position so that yoke 280, 282 interrupts the beam of light between diode 288 and detector 290. At this point, holder 260 can be moved into or out of position relative to plunger 223, so that a variety of such holders 260 can be sequentially positioned, particularly if each one is supplied with a reagent pre-attached to the inside wall of the cup. (Such a reagent can be, e.g., an antibody specific to a particular analyte.)

Figures 6, 7:
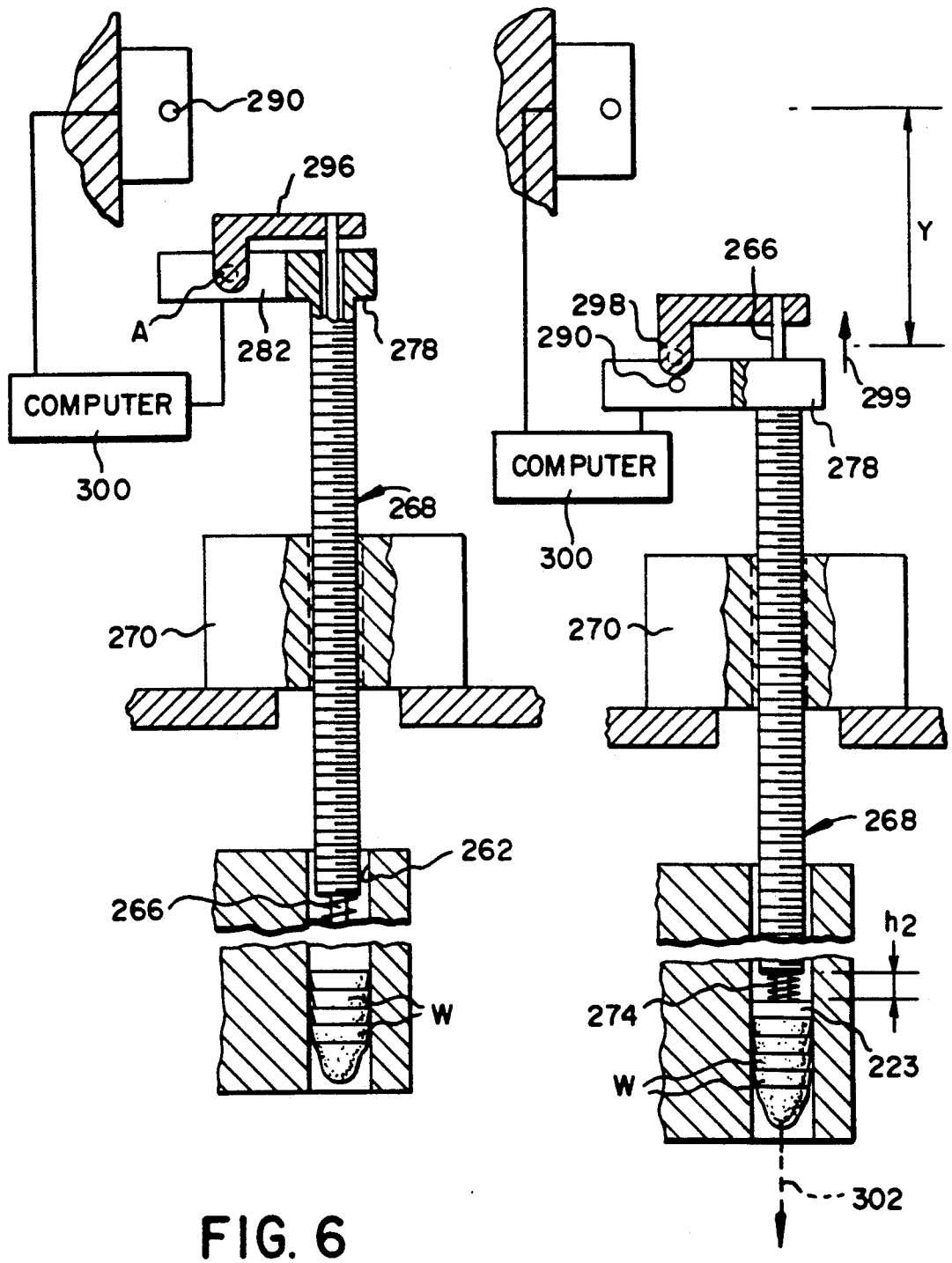
FIGS. 6 and 7 are elevational views similar to that of FIG. 4, but of the plunger and sensors positioned in other than their "home" positions.

As linear actuator 270 causes housing 268 to advance downwardly, FIG. 6, yoke 280,282 uncovers detector 290 and a signal is registered on computer 300 that plunger movement has started. The number of steps used by the stepper motor of linear actuator 270, and hence the linear advance of housing 268 into aperture 262 is then counted. At this point in time, plunger 223 (not shown) on rod 266 has not yet encountered the stack of cups W, so that portion 298 of flag 296 still interrupts the beam of light generated at "A" by collar 278.

Once plunger 223 does contact the top of the stack, FIG. 7, rod 266 ceases advancing even though housing 268 continues. Hence, spring 274 starts to compress, and most importantly, portion 298 of flag 296 uncovers, arrow 299, detector 290, sending a signal to computer 300 to stop advancing housing 268 and that the stack has been contacted.

Calibration steps are used initially to determine and sense, using the plunger, that a) holder 260 is present and b) how far down within aperture 262 the top of a complete, unemptied stack is located. Thereafter, by calculating the distance Y, FIG. 7, as a difference in terms of movement of housing 268 between sensor events, computer 300 easily determines the number of cups W already used, and by subtraction, the number remaining.

To eject a cup W, either the spring 274 is used to generate a sufficient force when compressed from height $h_1$, FIG. 4, to height $h_2$, FIG. 7, to eject a cup past seal lip 264, FIG. 4, or an additional advance is given to housing 268 to bottom out on plunger 223 so as to force out a cup, arrow 302.

As an alternative to spring 274, a leaf spring 310, shown in phantom, FIG. 4, can be used to bias plunger 223 downwardly beyond its housing. In that case, cup ejection is achieved by bottoming out housing 268 onto plunger 223.

As yet another alternative, a septum 320 can be located above each uppermost cup W' in a stack, FIG. 8, to preserve and protect any reagent pre-attached to that uppermost cup. The septum simply rests on the top edge of cup W'. If used, the septum remains in place between cup W' and the plunger, much as an anti-backup platen does in the cartridge in the embodiment of FIG. 1. If septum 320 is not used, then cup W' can be used as a "septum", in which case preferably it is not supplied with a reagent pre-attached and is not used to conduct an assay.

As yet another variation, it will be readily apparent that the positions of the sensor diode-detector, and flag, can be reversed, so that, e.g., finger 296 becomes a sensing yoke on plunger 266, and collar 278 provides a flag that fits within such a yoke, FIG. 5. Similarly, portion 292 on the analyzer can be a finger that breaks a beam of light generated between sensors on yoke 280,282.

The invention disclosed herein may be practiced in the absence of any element which is not specifically disclosed herein.

The invention has been described in detail with particular reference to certain preferred embodiments thereof, but it will be understood that variations and modifications can be effected within the spirit and scope of the invention.

What is claimed is:

1. In an analyzer for detecting analytes in a patient liquid deposited into a test element, the analyzer comprising a source of test elements including means for providing the test elements in stack, a plunger for moving the stack linearly to a test element dispensing location, a driver operatively connected to said plunger to drive said plunger to and away from said stack, said driver including means for converting rotary motion into linear motion, and a patient liquid depositor for depositing liquid into a dispensed test element;

the improvement wherein said plunger further includes a housing within which said plunger is reciprocatingly mounted for linear movement, and biasing means for biasing said plunger to move into said housing against the action of said biasing means, a portion of said driver being mounted on said housing; and a first sensing means for sensing when said plunger has moved into said housing against the action of said biasing means, so that a signal can be generated that said plunger has encountered said stack.

2. An analyzer as defined in claim 1, wherein said sensing means comprises a sensor fixed to said housing and a flag fixed to sad plunger, said biasing means being effective to normally push said plunger and said flag to and from a predetermined detection position.

3. An analyzer as defined in claim 2, wherein said biasing means acts to push said plunger and said flag out of detection by said sensor, and further including a second sensor comprising a flag fixed to said analyzer at a position effective to be detected by said sensor when said housing is in a "home" position.

4. An analyzer as defined in claim 1, wherein said housing-mounted portion of said driver comprises a rack gear, and said driver further includes a pinion gear meshed with said rack gear for linearly moving said rack gear, housing and said plunger.

5. An analyzer as defined in claim 1, wherein aid test elements are slide test elements, and further including in said analyzer, a slide element dispenser for dispensing a slide element from the stack at said dispensing location.

6. An analyzer as defined in claim 5, wherein said movement of said plunger against said biasing means is effective to generate a uniform force to uniformly bias each of said slide element in said stack into said dispensing location.

7. An analyzer as defined in claim 1, wherein said movement of said plunger against said biasing means is effective to generate a uniform force to uniformly bias each of said test elements in said stack into said dispensing location.

8. An analyzer as defined in claim 1, wherein said housing comprises an externally threaded lead screw.

9. An analyzer as defined in claim 1, and further including means for counting the number of test elements remaining in said stack.

10. An analyzer as defined in claim 9, wherein said counting means comprises a second sensing means, wherein said second sensing means comprises at least one of (a) a second sensor and a second flag wherein said second sensor is fixed to said analyzer in a position to detect said housing when said housing is away from said stack; and (b) a second sensor and a second flag wherein said second sensor is mounted on said housing; and wherein said second means including a computer to calculate the number of test elements that can fit within the distance represented by said second means being triggered by movement of said second flag relative to said second sensor.

* * * * *

UNITED STATES PATENT AND TRADEMARK OFFICE
CERTIFICATE OF CORRECTION

PATENT NO. : 5,271,896

DATED : December 21, 1993

INVENTOR(S) : Raymond F. Jakubowicz et al.

It is certified that error appears in the above-identified patent and that said Letters Patent is hereby corrected as shown below:

Column 7, line 1, Delete "sad" and insert – said–.

Column 7, line 16, Delete "aid" and insert –said–.

Signed and Sealed this

Twenty-fifth Day of October, 1994

Attest:

BRUCE LEHMAN

*Attesting Officer*  *Commissioner of Patents and Trademarks*